United States Patent
Merkel et al.

(10) Patent No.: US 11,638,864 B2
(45) Date of Patent: *May 2, 2023

(54) INSTRUCTIONAL SURFACE WITH HAPTIC AND OPTICAL ELEMENTS

(71) Applicant: CFPH, LLC, New York, NY (US)

(72) Inventors: Stephen Merkel, New York, NY (US); Jason Poulos, Commack, NY (US)

(73) Assignee: CFPH, LLC, New York, NY (US)

( * ) Notice: Subject to any disclaimer, the term of this patent is extended or adjusted under 35 U.S.C. 154(b) by 78 days.

This patent is subject to a terminal disclaimer.

(21) Appl. No.: 17/207,557

(22) Filed: Mar. 19, 2021

(65) Prior Publication Data

US 2021/0205690 A1 Jul. 8, 2021

Related U.S. Application Data

(63) Continuation of application No. 16/385,019, filed on Apr. 16, 2019, now Pat. No. 10,953,306, which is a
(Continued)

(51) Int. Cl.
*A63B 71/06* (2006.01)
*A63B 21/00* (2006.01)
(Continued)

(52) U.S. Cl.
CPC ........ *A63B 71/0622* (2013.01); *A61B 5/1116* (2013.01); *A61B 5/6892* (2013.01);
(Continued)

(58) Field of Classification Search
CPC ............ A63B 24/0062; A63B 24/0087; A63B 21/4037; A63B 71/0622; A63B 2220/51;
(Continued)

(56) References Cited

U.S. PATENT DOCUMENTS 3,006,644 A * 10/1961 Usher .................... A63B 23/02
116/222
3,258,266 A * 6/1966 Kamish .................... A63B 5/00
33/833
(Continued)

OTHER PUBLICATIONS

Gregory Han: "TERA: An Interactive fitness Yoga Mat That Poses As a Rug", Design Milk, Jun. 19, 2014 (accessed Apr. 23, 2021), https://design-milk.com/tera-interactive-fitness-feedback-yoga-mat/.
(Continued)

*Primary Examiner* — Garrett K Atkinson

(57) ABSTRACT

An exercise system may include an exercise mat; sensors integrated into the exercise mat, each of the sensors configured to sense when a force is applied to a respective portion of the exercise mat; and displays coupled to the exercise mat and configured to display indications corresponding to desired locations for body parts of a user in accordance with an exercise routine. On one or more of the displays, indications corresponding to desired locations of a user's body part may be displayed in accordance with a form of one of stored exercise routines; and one or more of the sensors may sense an application of force to the exercise mat. One or more of the displays may display at least one marker identifying a direction from a location of the sensed application of force to a display location of the at least one of the indications.

20 Claims, 11 Drawing Sheets

Related U.S. Application Data continuation of application No. 16/004,617, filed on Jun. 11, 2018, now Pat. No. 10,293,240, which is a continuation of application No. 15/007,563, filed on Jan. 27, 2016, now Pat. No. 9,993,715.

(51) Int. Cl.

| | | |
|---|---|---|
| *A61B 5/00* | (2006.01) | |
| *A61B 5/11* | (2006.01) | |
| *G06V 40/20* | (2022.01) | |
| *A63B 24/00* | (2006.01) | |
| *A63B 69/00* | (2006.01) | |

(52) U.S. Cl.
CPC ............ *A61B 5/744* (2013.01); *A61B 5/7455* (2013.01); *A63B 21/4037* (2015.10); *G06V 40/23* (2022.01); *A61B 2562/0247* (2013.01); *A61B 2562/046* (2013.01); *A63B 24/0087* (2013.01); *A63B 69/0002* (2013.01); *A63B 69/0024* (2013.01); *A63B 2071/0647* (2013.01); *A63B 2071/0655* (2013.01); *A63B 2071/0658* (2013.01); *A63B 2071/0675* (2013.01); *A63B 2071/0694* (2013.01); *A63B 2209/10* (2013.01); *A63B 2210/50* (2013.01); *A63B 2220/52* (2013.01); *A63B 2220/56* (2013.01); *A63B 2225/50* (2013.01); *A63B 2225/74* (2020.08); *A63B 2243/0025* (2013.01)

(58) Field of Classification Search
CPC .... A63B 2071/0675; A63B 2071/0647; A63B 21/0604; A63B 2024/0068; A63B 24/0075; A63B 2244/08; A63B 69/0002; A63B 69/0024; A63B 2071/0655; A63B 2071/0658; A63B 2071/0694; A63B 2209/10; A63B 2210/50; A63B 2220/52; A63B 2220/56; A63B 2225/50; A63B 2225/74; A63B 2243/0025; A61B 5/1116; A61B 5/6892; A61B 5/744; A61B 5/7455; A61B 2562/0247; A61B 2562/046; G06V 40/23

See application file for complete search history.

(56) References Cited

U.S. PATENT DOCUMENTS

| | | | | |
|---|---|---|---|---|
| 3,795,396 | A * | 3/1974 | Kropelnitski | A63B 5/16 116/202 |
| 4,208,050 | A * | 6/1980 | Perrine | A63B 5/16 473/447 |
| 4,323,234 | A * | 4/1982 | Glaese | A63B 5/16 116/335 |
| 4,693,598 | A * | 9/1987 | Sehr | G01S 3/78 33/293 |
| 4,932,137 | A * | 6/1990 | Haley | A63B 5/16 273/454 |
| 5,031,903 | A * | 7/1991 | Clarke | A63B 5/16 473/447 |
| 5,072,931 | A * | 12/1991 | Carlson | A63B 5/00 473/447 |
| 5,838,638 | A * | 11/1998 | Tipton | A63B 5/16 368/10 |
| 6,181,647 | B1 * | 1/2001 | Tipton | A63B 5/16 368/10 |
| 7,097,589 | B2 * | 8/2006 | Underwood | A63B 5/00 473/447 |
| 7,182,704 | B2 * | 2/2007 | Levy | A63B 69/0071 273/317.3 |
| 7,361,104 | B2 * | 4/2008 | Levy | A63B 69/0071 273/317.3 |
| 7,530,925 | B2 * | 5/2009 | Underwood | A63B 5/16 482/148 |
| 7,984,696 | B2 * | 7/2011 | Horrocks | A63K 3/046 119/705 |
| 8,025,606 | B2 * | 9/2011 | Hamilton | A63B 23/0244 434/247 |
| 9,017,222 | B2 * | 4/2015 | Hofeldt | A63B 5/00 482/15 |
| 2003/0054327 | A1 * | 3/2003 | Evensen | A63B 24/0003 434/252 |
| 2003/0077556 | A1 * | 4/2003 | French | A61B 5/1113 434/258 |
| 2005/0069853 | A1 * | 3/2005 | Tyson | A61B 5/0002 434/247 |
| 2005/0130772 | A1 * | 6/2005 | Levy | A63B 69/0071 473/433 |
| 2005/0153265 | A1 * | 7/2005 | Kavana | G09B 19/0015 434/250 |
| 2006/0019737 | A1 * | 1/2006 | Yang | G07F 17/32 463/19 |
| 2006/0154220 | A1 * | 7/2006 | Toniolo | G09B 19/0015 434/250 |
| 2006/0258515 | A1 * | 11/2006 | Kang | A63B 69/00 482/83 |
| 2007/0129180 | A1 * | 6/2007 | Levy | A63B 69/0071 473/415 |
| 2010/0129780 | A1 * | 5/2010 | Homsi | A63B 24/0062 434/258 |
| 2010/0267453 | A1 * | 10/2010 | Fujishima | A63B 23/0244 463/35 |
| 2010/0323800 | A1 * | 12/2010 | Inubushi | A63F 13/08 463/43 |
| 2011/0118018 | A1 * | 5/2011 | Toyoda | A63B 24/0003 463/31 |
| 2012/0058861 | A1 * | 3/2012 | Satut | A63B 6/00 482/8 |
| 2012/0130514 | A1 * | 5/2012 | Homsi | A63B 24/0062 700/91 |
| 2012/0130515 | A1 * | 5/2012 | Homsi | G06F 19/00 700/91 |
| 2012/0143358 | A1 * | 6/2012 | Adams | G06F 3/011 700/92 |
| 2012/0283080 | A1 * | 11/2012 | Mayr | A63B 23/0244 482/142 |
| 2013/0011819 | A1 * | 1/2013 | Horseman | A61B 5/6887 434/257 |
| 2014/0011555 | A1 * | 1/2014 | McGhee | A63F 13/212 463/7 |
| 2014/0074265 | A1 * | 3/2014 | Arginsky | A63B 71/0622 700/91 |
| 2015/0364059 | A1 | 12/2015 | Marks | |
| 2017/0050096 | A1 * | 2/2017 | Bentley | A63B 69/00 |
| 2017/0094306 | A1 * | 3/2017 | Jia | H04N 19/597 |
| 2019/0001213 | A1 | 1/2019 | Merket et al. | |
| 2019/0304239 | A1 | 10/2019 | Gelman et al. | |

OTHER PUBLICATIONS

Melissa Malamut: "MIT Students Created a Light up Yoga Mat", Boston Magazine, Feb. 6, 2014 (accessed 0/23/2021), https://www.bostonmagazine.com/health/2014/02/06/light-yoga-mat/.

Xtreme fit Personal trainer for the whole family, Games sport pakage & exercise mat, User Manual , Jul. 2009.

\* cited by examiner

INSTRUCTIONAL SURFACE WITH HAPTIC AND OPTICAL ELEMENTS

CROSS REFERENCE TO RELATED APPLICATION

This application is a continuation of U.S. patent application Ser. No. 16/385,019 filed on Apr. 16, 2019 which is a continuation of U.S. patent application Ser. No. 16/004,617 filed Jun. 11, 2018 (now U.S. Pat. No. 10,293,240 issued on May 21, 2019), which is a continuation of U.S. patent application Ser. No. 15/007,563 filed Jan. 27, 2016 (now U.S. Pat. No. 9,993,715 issued on Jun. 12, 2018), the disclosures of which are hereby incorporated by reference herein in their entireties.

FIELD

Some embodiments may relate to surfaces including, for example, exercise mats.

BACKGROUND

An exercise mat provides a user with support, grip, and cushioning when the user is exercising on a hard surface such as a wood, tile, or concrete floor. Exercise using an exercise mat is typically performed in a group setting, such as a gym class, or on an individual basis, such as at home, in the park, or any other location. Depending on a user's skill level, the user may require varying levels of instruction to perform the forms or motions of an exercise routine properly. For example, in the group setting, an instructor performs the routine for the class, acting as a model that each user then attempts to follow or duplicate. The instructor may also move about the class and correct individual users during the session.

SUMMARY

The following should be understood as embodiments and not claims.

An exercise system comprising: an exercise mat; a plurality of sensors integrated into the exercise mat, each of the sensors configured to sense when a force is applied to a respective portion of the exercise mat; a plurality of displays coupled to the exercise mat and configured to display indications corresponding to desired locations for body parts of a user in accordance with an exercise routine; at least one processor disposed in communication with the plurality of sensors and the plurality of displays; and memory storing at least one exercise routine for use with the exercise mat and instructions that, when executed by the at least one processor, configures the exercise system to: display on one or more of the displays indications corresponding to desired locations of a user's body part in accordance with a form of one of the exercise routines stored in memory; sense by one or more of the sensors an application of force to the exercise mat; determine that a location of the sensed application of force is different than a display location of at least one of the indications; and display on one or more of the displays at least one marker identifying a direction from the location of the sensed application of force to the display location of the at least one of the indications.

The system above, wherein the instructions, when executed by the at least one processor, further configure the exercise system to: sense by one or more of the sensors a change in the location of the application of force to the exercise mat; determine that the changed location corresponds to the display location of at least one of the indications; and display on one or more of the displays an indication of a match between the changed location and the display location of at least one of the indications. The system above, wherein the displays are embedded into a surface of the exercise mat. The system above, wherein the exercise mat further includes a mesh, and wherein the displays are secured to the mesh. The system above, wherein the mesh is embedded into a surface of the exercise mat. The system above, wherein a surface of the exercise mat is covered by a transparent layer, and wherein the displays are disposed between the surface of the exercise mat and the transparent layer. The system above, wherein the markers are in an inactive state when the location of the sensed application of force corresponds to the location of the at least one of the indications. The system above, wherein the markers are transparent when in the inactive state. The system above, wherein the markers are not displayed on the displays when in the inactive state. The system above, wherein at least one of the markers is transitioned to an active state when the location of the sensed application of force is different from the location of the at least one of the indications. The system above, wherein the at least one of the markers is displayed on the displays when in the active state. The system above, wherein the at least one of the markers is highlighted when in the active state. The system above, wherein the plurality of indications include an outline of a body part. The system above, in which the system comprises a projector, and in which the at least one processor is configured to cause the projector to project a display indicating a positional adjustment of the user.

A method comprising: causing, by at least one processor in communication with a plurality of displays coupled to an exercise mat, the display of indications on one or more of the displays, the indications corresponding to desired locations of a user's body part in accordance with a form of an exercise routine stored in memory associated with the at least one processor; sensing an application of force to the exercise mat by one or more sensors integrated into the exercise mat and configured to sense when a force is applied to a respective portion of the exercise mat, the sensors disposed in communication with the at least one processor; determining, by at least one processor, that a location of the sensed application of force is different than a display location of at least one of the indications; and displaying on one or more of the displays at least one marker identifying a direction from the location of the sensed application of force to the display location of the at least one of the indications.

The method above, further comprising: sensing by one or more of the sensors a change in the location of the application of force to the exercise mat; determining that the changed location corresponds to the display location of at least one of the indications; and displaying an indication of a match between the changed location and the display location of at least one of the indications on one or more of the displays. The method above, wherein the displays are embedded into a surface of the exercise mat. The method above, wherein the exercise mat further includes a mesh, and wherein the displays are secured to the mesh. The method above, wherein the mesh is embedded into a surface of the exercise mat. The method above, wherein a surface of the exercise mat is covered by a transparent layer, and wherein the displays are disposed between the surface of the exercise mat and the transparent layer. The method above, wherein the markers are in an inactive state when the location of the sensed application of force corresponds to the location of the at least one of the indications. The method above, wherein the markers are transparent when in the inactive state. The method above, wherein the markers are not displayed on the displays when in the inactive state. The method above, wherein at least one of the markers is transitioned to an active state when the location of the sensed application of force is different from the location of the at least one of the indications. The method above, wherein the at least one of the markers is displayed on the displays when in the active state. The method above, wherein the at least one of the markers is highlighted when in the active state. The method above, wherein the plurality of indications include an outline of a body part.

An exercise system comprising: an exercise mat; a plurality of actuating mechanisms disposed in the exercise mat, each actuating mechanism actuatable to deform at least a portion of the exercise mat corresponding to desired locations for body parts of a user in accordance with an exercise routine; at least one processor disposed in communication with the plurality of sensors and the plurality of actuating mechanisms; and memory storing at least one exercise routine for use with the exercise mat and instructions that, when executed by the at least one processor, configures the exercise system to: actuate one or more of the actuating mechanisms to cause a deformation in the exercise mat corresponding to desired locations of a user's body part in accordance with a form of one of the exercise routines stored in memory.

The exercise system above, wherein the deformation is an indentation in a surface of the exercise mat. The exercise system above, wherein the actuating mechanisms include bladders. The exercise system above, further comprising: at least one pump in fluid communication with at least one of the bladders, wherein the instructions, when executed by the at least one processor, further configure the system to: activate the at least one pump to supply or withdraw fluid from at least one of the bladders to cause the deformation corresponding to the desired location of the user's body part. The exercise system above, wherein the actuating mechanisms are actuators. The exercise system above, wherein the actuators are selected from the group consisting of solenoids, electric motors, hydraulic motors, and pneumatic motors. The exercise system above, further comprising: a plurality of sensors integrated into the exercise mat, each of the sensors configured to sense when a force is applied to a respective portion of the exercise mat. The exercise system above, wherein the instructions, when executed by the at least one processor, further configure the system to: sense by one or more of the sensors an application of force to the exercise mat; determine that a location of the sensed application of force is different than a location of the deformation; and actuate one or more of the actuating mechanisms to cause a deformation in the exercise mat identifying a direction from the location of the sensed application of force to the location of the deformation corresponding to the desired location of the user's body part. The exercise system above, wherein the instructions, when executed by the at least one processor, further configure the system to: sense by one or more of the sensors an application of force to the exercise mat; determine a weight distribution of a user based at least in part on the sensed application of force; and actuate one or more of the actuating mechanisms to cause a deformation in the exercise mat at a location corresponding to a location of the sensed application of force, the deformation applying an additional force to a body part of the user applying the sensed application of force to the exercise mat, the amount of additional force being based at least in part on the determined weight distribution. The exercise system above, wherein the instructions, when executed by the at least one processor, further configure the system to: sense a change in the application of force to the exercise mat; determine a change to the weight distribution of the user based at least in part on the sensed change in the application of force to the exercise mat; and adjust the amount of additional force applied by the actuating mechanisms by an amount corresponding to the determined change to the weight distribution of the user. The exercise system above, wherein the additional force is applied periodically. The exercise system above, wherein rate at which the additional force is applied is based at least in part on a difference between the determined weight distribution of the user and a desired weight distribution of the user in accordance with the form of the exercise routine. The exercise system above, wherein the rate at which the additional force is applied is increased or decreased as the difference between the determined weight distribution of the user and the desired weight distribution of the user increases or decreases respectively.

A method comprising: actuating one or more actuating mechanisms disposed in an exercise mat, the actuation of the one or more actuating mechanisms causing a deformation in the exercise mat corresponding to desired locations of a user's body part in accordance with a form of an exercise routine stored in memory. The method above, wherein the deformation is an indentation in a surface of the exercise mat. The method above, wherein the actuating mechanisms include bladders. The method above, further comprising: activating at least one pump to supply or withdraw fluid from at least one of the bladders to cause the deformation corresponding to the desired location of the user's body part. The method above, wherein the actuating mechanisms are actuators. The method above, wherein the actuators are selected from the group consisting of solenoids, electric motors, hydraulic motors, and pneumatic motors. The method above, further comprising: sensing by one or more sensors integrated into the exercise mat an application of force to the exercise mat, each of the sensors configured to sense when a force is applied to a respective portion of the exercise mat; determining that a location of the sensed application of force is different than the location of the deformation; and actuating one or more of the actuating mechanisms to cause a deformation in the exercise mat identifying a direction from the location of the sensed application of force to the location of the deformation corresponding to the desired location of the user's body part. The method above, further comprising: sensing by one or more of the sensors an application of force to the exercise mat; determining a weight distribution of a user based at least in part on the sensed application of force; and actuating one or more of the actuating mechanisms to cause a deformation in the exercise mat at a location corresponding to a location of the sensed application of force, the deformation applying an additional force to a body part of the user applying the sensed application of force to the exercise mat, the amount of additional force being based at least in part on the determined weight distribution. The method of claim above, further comprising: sensing a change in the application of force to the exercise mat; determining a change to the weight distribution of the user based at least in part on the sensed change in the application of force to the exercise mat; and adjusting the amount of additional force applied by the actuating mechanisms by an amount corresponding to the determined change to the weight distribution of the user. The method above, wherein the additional force is applied periodically. The method above, wherein rate at which the additional force is applied is based at least in part on a difference between the determined weight distribution of the user and a desired weight distribution of the user in accordance with the form of the exercise routine. The method above, wherein the rate at which the additional force is applied is increased or decreased as the difference between the determined weight distribution of the user and the desired weight distribution of the user increases or decreases respectively.

FIGURES

DETAILED DESCRIPTION

The following embodiments and aspects of the present disclosure provide users with instructional feedback in performing motions, forms, poses, or other exercise related activities. During an exercise class or individual exercise session it is often difficult for a user to follow an instructor or an instructional video while attempting to perform the form or motion that the particular exercise requires. This is because the user is required to watch the instructor instead of focusing on performance of the motion or form itself. For example, when the exercise routine requires the user's head to be in a downward position, for example, downward dog in yoga, the user's field of view typically will not include the instructor, television, tablet, phone, etc. In order for a user receive further instruction, the user will need to raise his or her head thereby ruining the very form or motion that he is trying to perform. Thus, it is often difficult for a user to learn the proper positions and forms of an exercise routine while constantly attempting to track and watch the instructor. In a large class, for example, the user may not even receive any one on one attention from the instructor and may instead be left to flounder around while attempting to perform the various motions or forms of the exercise routine with little to no direct instruction at all. Likewise, in an individual exercise session, the instructor on the video provides no feedback on the user's motions or forms. This lack of direct instruction may lead to incorrect motions or forms and possibly compromise the health of the user with injuries.

Figure 1:
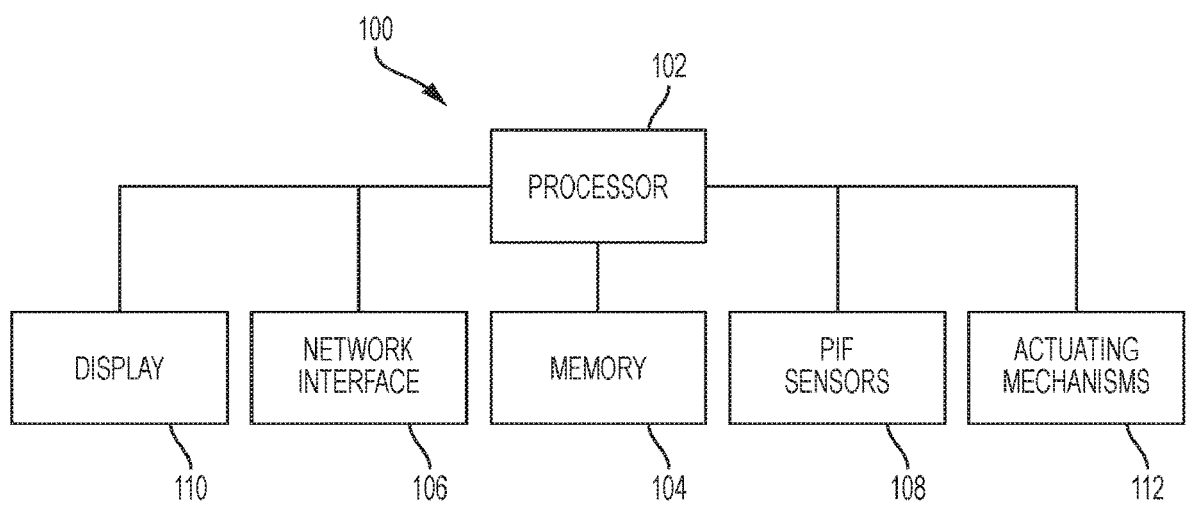
FIG. 1 is a schematic view of an exercise system according to an embodiment of the present disclosure.
Figure 2:
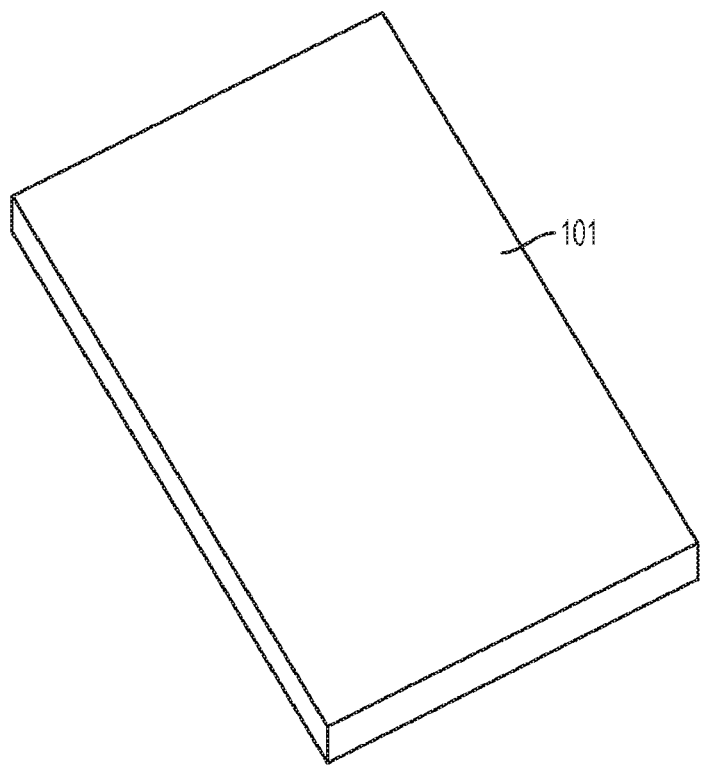
FIG. 2 is a top, plan view of an exercise mat according to an embodiment of the exercise system of FIG. 1.

FIG. 1 illustrates an example of an exercise system 100 that may be used in some embodiments. Exercise system 100 may include at least one processor 102, memory 104, a network interface 106, and pressure/force (P/F) sensors 108. In some embodiments, exercise system 100 may also include, for example, one or more displays 110, and/or one or more actuating mechanisms 112. In some embodiments, exercise system 100 may include an exercise mat 113 as illustrated, for example, in FIGS. 2 and 3.

Processor 102 may include one or more microprocessors, central processing units (CPUs), computing devices, microcontrollers, digital signal processors, or like devices or any combination thereof, regardless of the architecture (e.g., chip-level multiprocessing/multi-core, RISC, CISC, Microprocessor without Interlocked Pipeline Stages, pipelining configuration, simultaneous multithreading) that is configured to receive instructions, for example, from memory 104, and execute the instructions, thereby performing one or more processes defined by the instructions.

Memory 104 may be any computer-readable medium, a plurality of the same, or a combination of different media, capable of storing instructions, data, or other digital information. Memory 104 may include, for example, non-volatile media and volatile media. Non-volatile media include, for example, optical or magnetic disks and other persistent memory. Volatile media include dynamic random access memory (DRAM), which typically constitutes the main memory. Memory 104 may include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a processor can read data. Memory 104 may store instructions which when executed by processor 102 configure processor 102 to perform one or more processes. Memory 104 may also store one or more exercise routines which when executed by processor 102 configure processor 102 to provide a user of exercise system 100 with instructions for performing the one or more exercise routine in accordance with the following embodiments.

Network interface 106 is configured to communicate with external devices including, for example, cell phones, tablets, computers, servers, or other computing devices, via any wired or wireless medium including, for example, the Internet, LAN, WAN, Ethernet, Token Ring, telephone line, cable line, radio channel, optical communications line, commercial on-line service providers, bulletin board systems, satellite communications link, Bluetooth, WIFI, other similar methods of electronic communication, or any combination thereof.

P/F sensors 108 may be any pressure or force sensors that are configured to sense when pressure or force is applied to exercise mat 113. P/F sensors 108 may include force-sensing resistors, such as, for example, a conductive polymer or ink, pressure sensors, such as, for example, piezoelectric, capacitive, electromagnetic, optical, potentiometric, or other similar sensors that can detect the position of a user's body part or an amount of force being exerted by the users body part on exercise mat 113.

Displays 110 may be plasma, LCD, LED, or other similar types of displays capable of performing the functions described in more detail below. Displays 110 may be touch sensitive.

Actuating mechanisms 112 may be solenoids, electric motors, bladders, or other similar actuating mechanisms capable of performing the functions described in more detail below.

Figure 3:
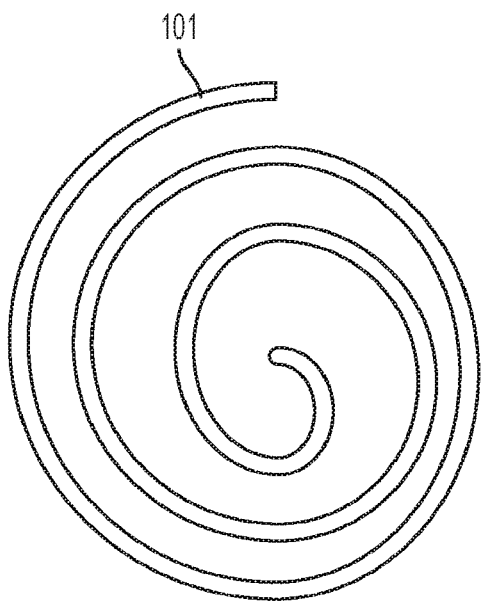
FIG. 3 is a side view the exercise mat of FIG. 2, illustrated in a rolled up configuration.

Exercise mat 113 may be formed of, for example, foam, rubber, carpet, vinyl, plastic, or other similar materials and may come in a variety of sizes and thicknesses depending on the intended use. As illustrated in FIG. 3, exercise mat 113 may be flexible or bendable such that exercise mat 113 may be folded or rolled up for transport and storage.

The following aspects and embodiments of exercise system 100 provide solutions for users requiring assistance and instruction during an exercise routine.

Exercise Mat with Screen

Figure 4:
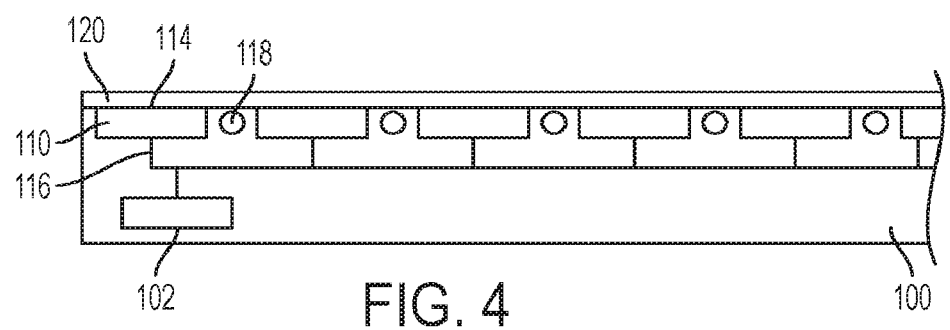
FIG. 4 is a side, cut away view, of an exercise mat according to an embodiment of the present disclosure.
Figure 5:
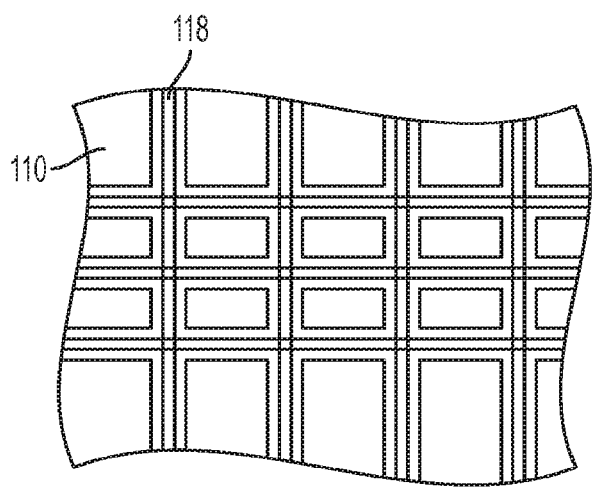
FIG. 5 is a top, plan view of the exercise mat of FIG. 4.

Referring now to FIGS. 4 and 5, in some embodiments, exercise system 100 includes a plurality of displays 110 embedded within, positioned on, or adjacent to a surface 114 of exercise mat 113. In some embodiments, displays 110 may be sized such that exercise mat 113 includes a large number of displays 110. For example, exercise mat may include fifty displays 110, one-hundred displays 110, two-hundred displays 110, or any desired number of displays 110. Displays 110 may be, for example, one square inch in size, two square inches in size, or any similar size suitable for allowing exercise mat 113 to include the desired number of displays 110. In some embodiments, exercise mat 113 may include a single display 110 formed of a plurality of individual LEDs such that the LEDs may be independently activated or activated in groups to provide the features described below. Displays 110 may be configured such that exercise mat 113 may be rolled up or folded for storage or transportation. One example display technology that may be used to facilitate a display of this type may include an Organic Light Emitting Diode.

Displays 110 may be embedded into surface 114 of exercise mat 113 or may be secured to surface 114, for example, by adhesive, snap clips, fasteners, or other similar forms of attachment. One or more wires 116 may electrically connect displays 110 to processor 102. Alternatively, displays may wirelessly communicate with processor 102, for example, via Bluetooth, WIFI, or other commonly used forms of wireless communication.

Referring now to FIG. 5, in some embodiments, exercise mat 113 may include a mesh 118. Mesh 118 is configured to receive displays 110 and provide structural support to displays 110. Mesh 118 may include, for example, wires, cables, or other reinforcing members 120. Displays 110 may be secured to mesh 118, for example, by adhesive, snap clips, fasteners, or other similar forms of attachment. Mesh 118 and displays 110 may together be embedded into surface 114 of exercise mat 113. Reinforcing members 120 may be formed of metals, plastics, or other similar materials. In some embodiments, reinforcing members 120 may be sufficiently flexible to allow exercise mat 113 to bend or flex.

In some embodiments, reinforcing members 120 may be sufficiently flexible to allow exercise mat 113 to be rolled up for storage or transportation. In some embodiments, mesh 118 provides an additional surface for receiving the weight of a user in addition to displays 110, for example, to reduce an amount of force applied directly to each of displays 110.

In some embodiments, displays 110 and/or mesh 118 may be covered or sealed by a surface layer 120. Surface layer 120 may be configured to provide a user of exercise mat 113 with additional traction, moisture wicking, or other similar features. Surface layer 120 may be formed from, for example, foam, silicone, rubber, or other similar materials. Surface layer 120 may be formed of a material that is configured to absorb liquids such as sweat, water, sports drinks, or condensation. In some embodiments, surface layer 120 may be formed of a translucent or transparent material.

Figure 6:
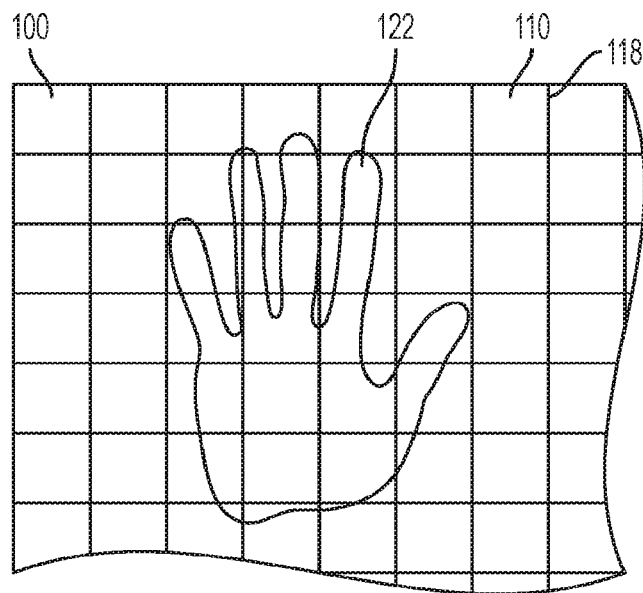
FIG. 6 is a top, plan view of the exercise mat of FIG. 4 illustrating an indication.
Figure 7:
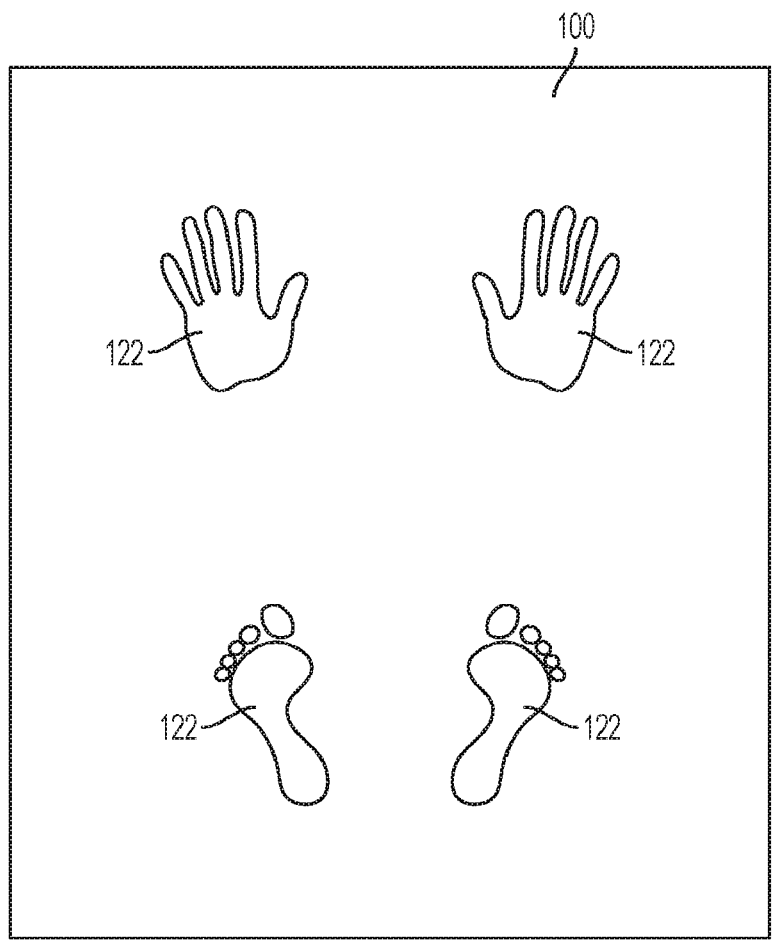
FIG. 7 is a top, plan view of the exercise mat of FIG. 4 illustrating multiple indications.

Displays 110 are configured to present a user with indications 122 of where a user is supposed to locate their hand, foot, fingers, knees, etc. for each form or position during an exercise routine. For example, as shown in FIG. 6, during an exercise routine, processor 102 may cause one or more of displays 110, to together present an indication 122, for example, an image of a left hand, to a user on exercise mat 113. The user may then use the indication 122 to assist the user in achieving the proper placement of the left hand for the current form or position of the exercise. For example, the user may place their left hand on top of the indication 122. As further illustrated in FIG. 7, displays 110 may, for example, display indications 122 for each hand and/or foot for assisting the user in achieving proper placement of hands and feet for the current form. Although indications 122 are mentioned with reference to hands and feet, indications 122 may also refer to any other body part. In some embodiments, indications 122 may additionally or alternatively include symbols, colors, or other similar features that indicate a location on the exercise mat 113 to a user.

Once a user has positioned their body part, such as their hands, feet, etc. on exercise mat 113, P/F sensors 108 may transmit a signal or other communication to processor 102 including data representing a location of the user's body part on exercise mat 113. In response to the received data, processor 102 may cause displays 110 to present indicators 124 to the user to provide the user with a direction in which to move the body part to align the body part with the proper placement for the exercise.

Figure 8:
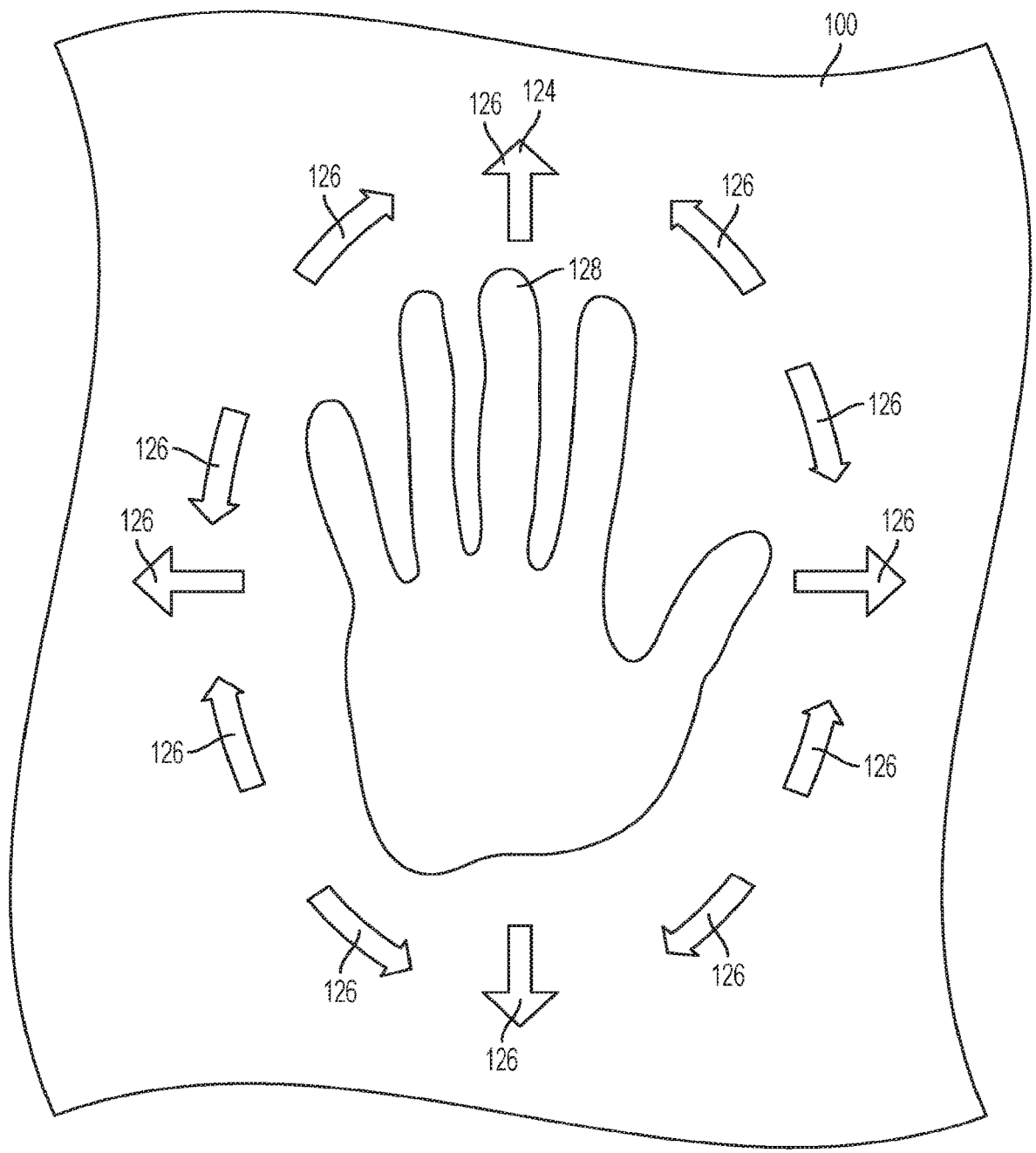
FIG. 8 is a top, plan view of a portion of the exercise mat of FIG. 4, illustrating directional indicators.

As shown in FIG. 8, in some embodiments, indicators 124 may include directional markers 126 such as, for example, arrows indicating a direction in which the user may move the body part 128 to achieve the proper placement of the body part for the current form or position of the exercise routine. Directional markers 126 may include forward and backwards arrows, left and right arrows (i.e. side to side), rotational arrows, or any other element indicating a direction. Depending on the location of the user's body part 128, as sensed by pressure/force sensors 108, one or more of directional markers 126 may or may not be presented by displays 110. For example, if the user's body part 128 is in the correct position, i.e. at the location of indication 122 (FIG. 7), directional markers 126 may be in an inactive state and may not be displayed. On the other hand, if the user's body part 128 is not in the correct position, one or more of directional markers 126 may be transitioned to an active state and displayed to indicate a direction that the user should move their body part to achieve the correct position. For example, a forward arrow and a side arrow may both be transitioned to an active state and displayed to indicate that the user needs to move their body part both forward and to the side. As another example, where the user has a proper side to side location, the forward arrow alone may be activated and displayed. In an alternate embodiment, directional markers 126 may always be displayed around indications 122 (FIG. 7) or at the location of the user's body part 128, as sensed by P/F sensors 108, when in the inactive state. For example, directional markers 126 may be transitioned to the active state through the use of highlighting, color, blinking, motion, or other similar effects to draw attention to the active directional marker 126. While in the inactive state, on the other hand, directional markers 126 may, in some embodiments, be displayed as an outline, as a dull or dark color, in a faded state, in a partially transparent state, a fully transparent state, or other similar effects that indicate inactivity. If the location of the user's body part 128 needs to move forward to achieve the proper location on the exercise mat 113, for example, the forward directional marker 126 may be transitioned from the inactive state to the active state to draw the user's attention to this fact. In some embodiments, directional markers 126 may only be visible when they are in the active state.

Figure 9:
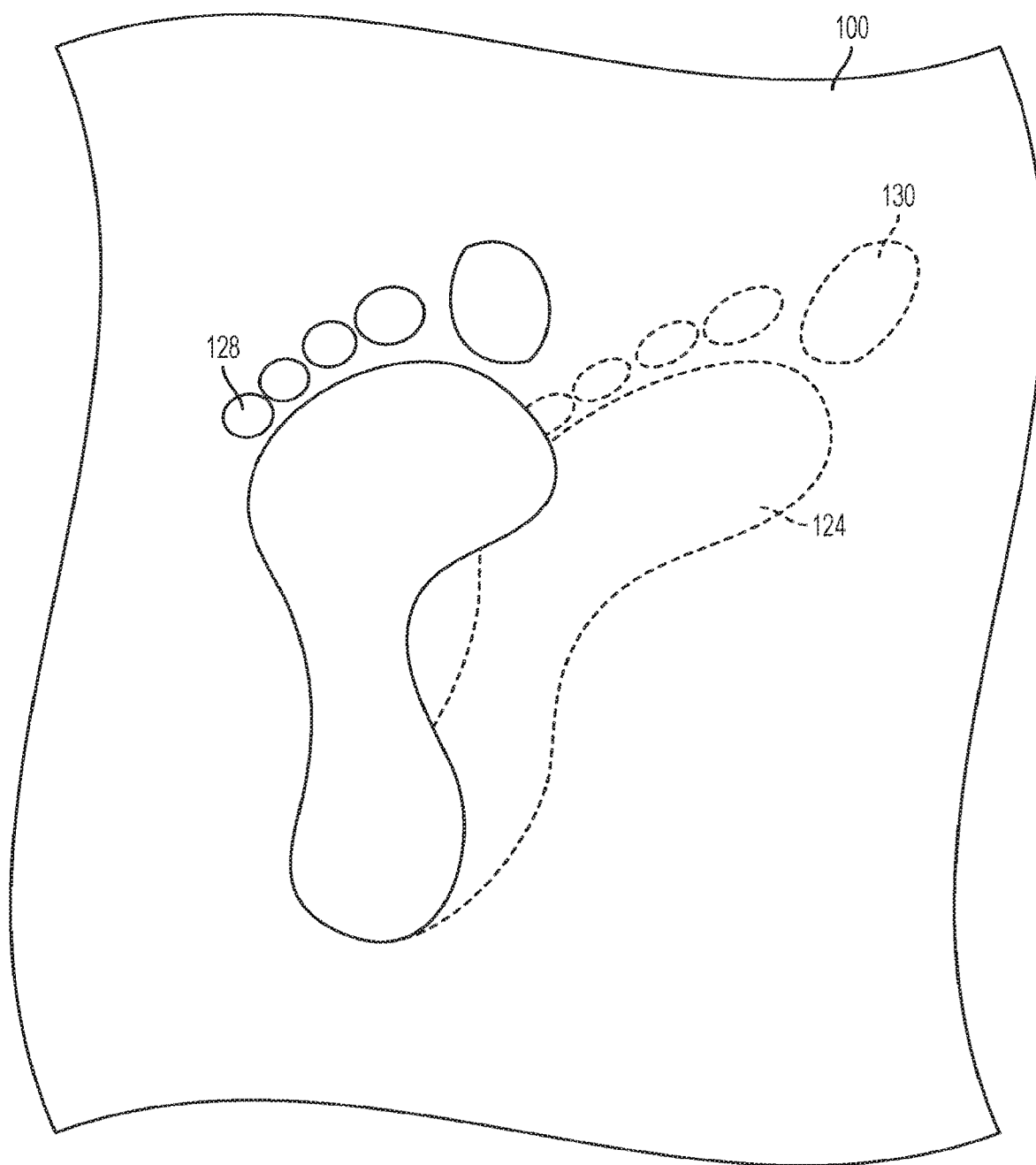
FIG. 9 is a top, plan view of a portion of the exercise mat of FIG. 4, illustrating an indicator including a partial outline.

As shown in FIG. 9, in some embodiments, indicators 124 may be presented as a partial outline 130 of the user's body part 128, in this example, a partial outline 130 of the body part 128 extending from the actual location of the user's body part 128. The outline 130 may be hashed, shaded, colored, or have other similar visual effects. For example, where the user has placed their body part 128 in a location that is offset slightly from the location of indication 122 (FIG. 7), partial outline 130 may provide the user with an indication of how to adjust their body part 128 to achieve the proper location for the form or position of the particular exercise.

Figure 10:
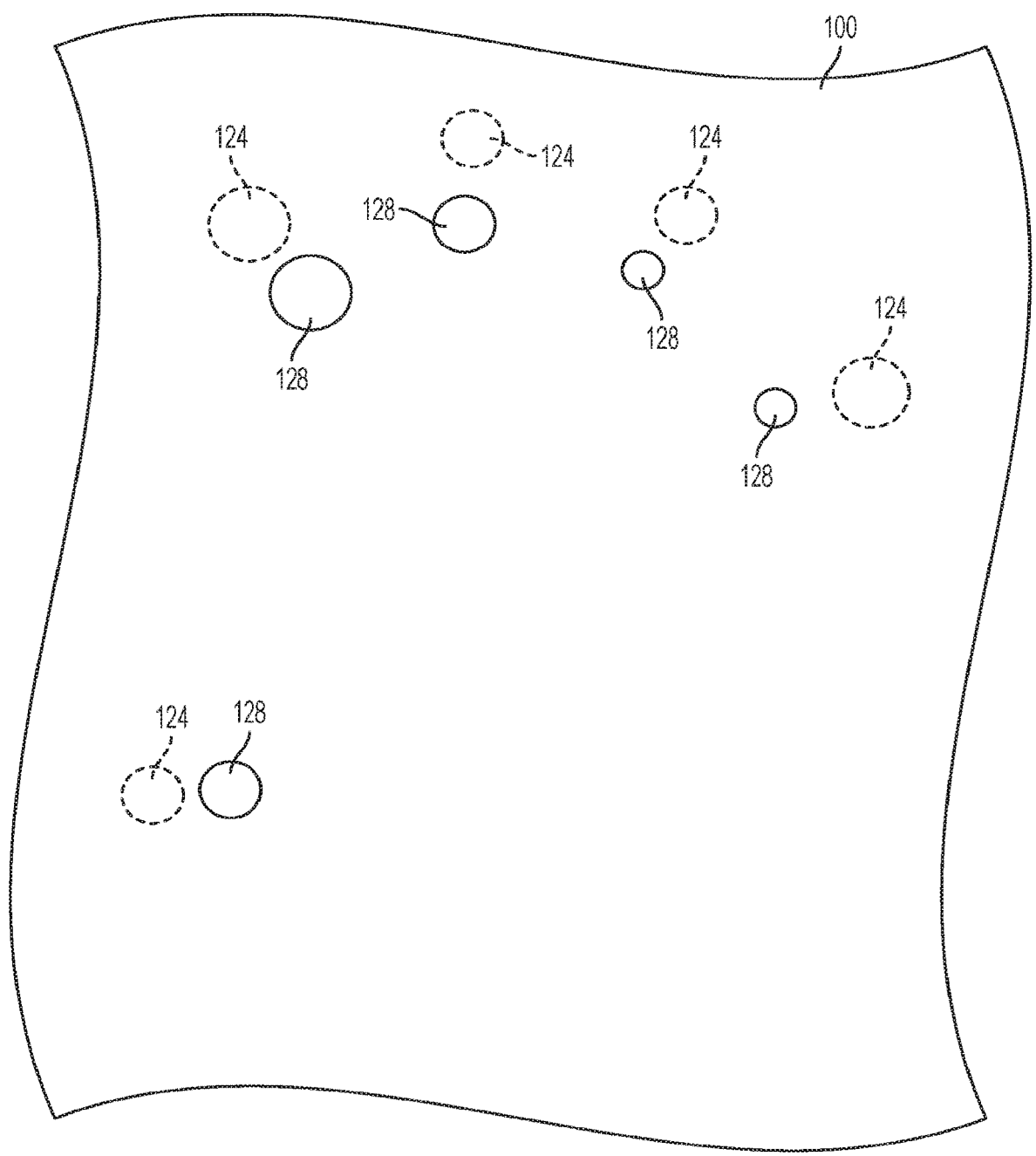
FIG. 10 is a top, plan view of a portion of the exercise mat of FIG. 4, illustrating indicators for finger tips.

In some embodiments, indicators 124 may be presented near a sensed location of the user's body part 128. As illustrated in FIG. 10, the location of body part 128 may be, for example, the location of the user's fingers, as sensed by P/F sensors 108, on exercise mat 113. Indicators 124 may be offset from the location of body part 128 and provide the user with an indication of how to position the body part 128 to achieve the proper location for the form or position of the particular exercise. For example, as illustrated in FIG. 10, indicators 124 may resemble finger tips and provide the user with an indication of where to position their fingers for the form or position that they are trying to achieve. Indicators 124 may also include textual or graphical information that describes or identifies the body part to be placed on the indicator 124. For example, one of indicators 124 may display the letters "RI", referring to the right index finger. Likewise, other letters or words may be used to describe the remaining fingers including, for example, "RM" (right middle), "RR" (right ring), "RP" (right pinky), "RT" (right thumb), or any other description of the body part to be placed on the indicators 124.

Exercise Mat with Tactile Feedback

Figure 11:
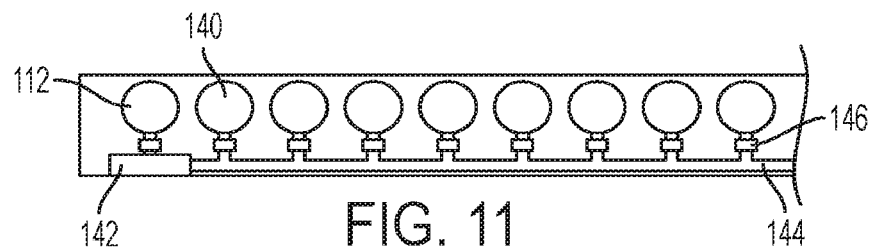
FIG. 11 is a side, cut away view, of an exercise mat according to an embodiment of the present disclosure.

In some embodiments, exercise system 100 includes actuating mechanisms 112, as illustrated, for example, in FIGS. 11-15, to provide the user with tactile feedback. As illustrated in FIG. 11, actuating mechanisms 112 may include bladders 140 embedded within exercise mat 113. Bladders 140 may be connected to a pump 142 via tubes 144. Each bladder 140 may be separately connected to pump 142 or may be connected to pump 142 in groups. In some embodiments, a valve 146 may be disposed between each bladder 140 and pump 142 to allow for each bladder 140 to be individually inflated or deflated. In some embodiments, bladders 140 may be grouped together where each group of bladders 140 has a single valve 146. In this manner, a group of bladders 140 may be inflated or deflated at the same time. Pump 142 and valves 146 may be electrically or wirelessly connected to processor 102 and controlled by processor 102 in accordance with a particular exercise routine. Bladders 140 and pump 142 may be filled with any fluid suitable for inflation or deflation of bladders 140 including, for example, air, CO2, water, or any other similar fluid.

Figure 12:
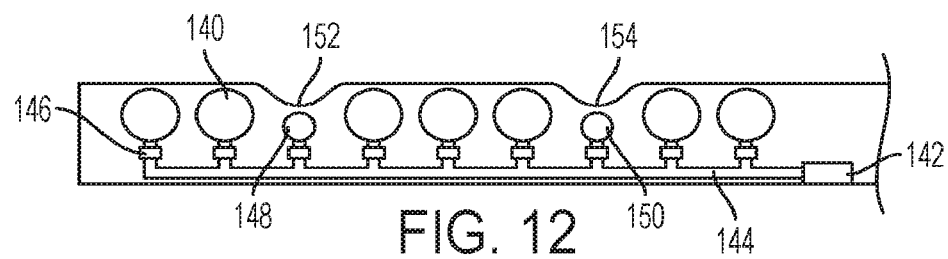
FIG. 12 is a side, cut away view, of the exercise mat according to FIG. 11, illustrating indentations formed by actuators.

As illustrated in FIG. 12, individual or groups of bladders 140 may be inflated or deflated with fluid to provide a user with a visual and tactile indication of where to position their body parts. For example, specific bladders 148 and 150 may be deflated by pump 142 to form indentations 152 and 154, respectively, in exercise mat 113. Indentations 152 and 154 provide a user of exercise mat 113 with a visual indication of where to position their body part. In addition, indentations 152 and 154 also provide a user with a tactile indication of where to position their body part. For example, during an exercise routine, a user of exercise mat 113 including bladders 140 may, without looking at exercise mat 113, quickly find the proper location for placement of their body part through the sense of touch alone by feeling indentations 152 and 154 to achieve the desired form or position. This allows the user to maintain the posture and position of their back and head while still locating their body part in the designated location to achieve the desired form or position.

Figure 13:
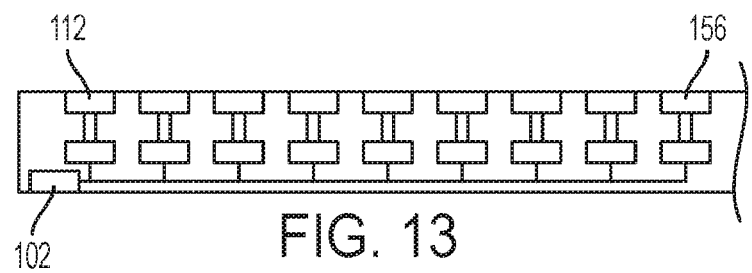
FIG. 13 is a side, cut away view, of an exercise mat according to an embodiment of the present disclosure.
Figure 14:
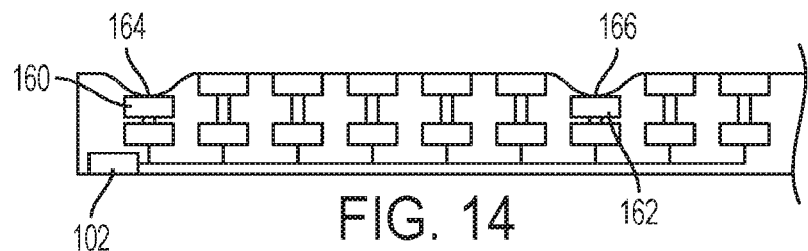
FIG. 14 is a side, cut away view, of the exercise mat according to FIG. 11, illustrating indentations formed by actuators.

In some embodiments, as illustrated in FIG. 13, actuating mechanisms 112 may include actuators 156. Actuators 156 may include, for example, solenoids, electric motors, hydraulic motors, pneumatic motors, or other similar actuators. Actuators 156 may be electrically connected to processor 102 via wires 158 or may alternatively be in communication with processor 102 via a wireless technology such as, for example, any of the wireless technologies described above. Actuators 156 may operate in a similar manner to bladders 140 as described above. For example, as illustrated in FIG. 14, specific actuators 160 and 162 of actuators 156 may be activated to cause indentations 164 and 166 respectively in exercise mat 113. Indentations provide a user with both visual and tactile feedback of the proper location for placement of a body part in a similar manner to that described above with respect to bladders 140.

Figure 15:
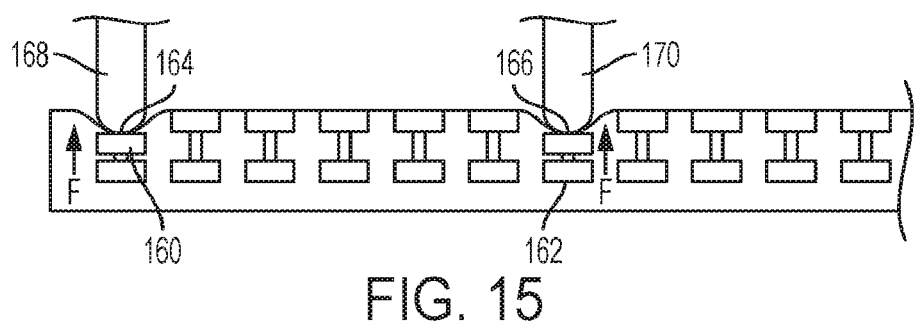
FIG. 15 is a side, cut away view, of the exercise mat according to FIG. 11, illustrating indentations formed by actuators and an additional force applied to a user's body part.

In some embodiments, as illustrated in FIG. 15, actuators 156 may also provide tactile feedback on the form or position of the exercise to a user. For example, P/F sensors 108 may be used to determine an amount of force being exerted on exercise mat 113 at the indentations 164 and 166 respectively by body parts 168 and 170. Processor 102 may then determine additional parameters such as, for example, the user's balance, weight distribution between body parts 168 and 170, and other similar parameters. If the processor 102 determines that the user's weight distribution does not match a desired weight distribution stored in memory 104 for the particular form or position, processor 102 may cause one or both of actuators 160 and 162 to exert an additional force F against the user's respective body parts 168 and 170. This additional force F provides the user with an indication that the user must adjust their weight distribution to comply with the particular form or position. As the user shifts their weight distribution between body parts 168, 170, or any other body part, the additional force F may be reduced until the user feels no additional force from actuators 160 and/or 162 when the user's weight distribution correctly matches the desired weight distribution for the particular form or position. For example, as the user shifts their weight distribution away from body part 160 and towards body part 170, the additional force F applied to body part 160 may be reduced. If the user shifts their weight distribution too far towards body part 170, the additional force F applied to body part 170 may be increased. In some embodiments, the additional force F may be a constant force against the user's body part until the user shifts their weight distribution to match the desired weight distribution for the particular form or position. Additional force F may alternatively be applied by bladders 140 instead of actuators 156.

In some embodiments, the additional force F may be applied periodically as a pulse, for example, a rapid pulse when the user's weight distribution is very far from the desired weight distribution for the particular form or position and a slow pulse when the user's weight distribution more closely matches the desired weight distribution for the particular form or position. As an exemplary non-limiting example, if the weight distribution has only a 20% match against the desired weight distribution for the particular form or position, processor 102 may cause additional force F to be pulsed at the user at a rate of fifty pulses per minute while if the weight distribution has an 80% match against the desired weight distribution for the particular form or position processor 102 may cause the additional force F to be pulsed at the user at a rate of ten pulses per minute. In some embodiments, it is contemplated that the rate of pulsing may vary with the percentage of a match to the desired weight distribution of the particular form or position. For example, the rate of pulsing may change linearly, exponentially, logarithmically, or any other desired rate of change as the percentage of a match increases or decreases. In some embodiments, the rate of pulsing may instead be static and have no correspondence to a percentage of match against the desired weight distribution for the particular form or position. Although example pulse rates are specified above, it is contemplated that the rate of pulsing may be greater than fifty pulses per minute, less than ten pulses per minute, between fifty and ten pulses per minute, or any other number of pulses per minute sufficient to indicate to the user that their weight distribution does not match the desired weight distribution of the particular form or position. In some embodiments the rate of pulsing may be any number of pulses per minute sufficient to indicate to the user how far from a match their weight distribution is when compared to the desired weight distribution of the particular form or position.

In some embodiments, exercise system 100 may include both displays 110 and actuating mechanisms 112 to provide the user may with both visual and tactile feedback when using exercise mat 113. For example, displays 110 may be disposed between actuating mechanisms 112 and surface 114 such that one or more of displays 110 may be indented by actuating mechanisms 112 to provide the user with tactile feedback. Alternatively, actuating mechanism 112 may be disposed between displays 110 and surface 114 to directly provide indentations to surface 114. In some embodiments, actuating mechanisms 112 may be transparent such that a user may be able to see displays 110 through actuating mechanisms 110.

A routine may be input into a processor element of a mat (e.g., through a network, from a memory, etc.). A program executed by the processor may cause a haptic and/or display element of a mat to operate to aid a user in working through the routine. The mat may cooperate with a sound or display device such as a television (e.g., by outputting information to the television, receiving information for a routine from the television, etc.). In some embodiments, a Bluetooth or other wireless network may allow a display and/or audio element to communicate with and synchronize a routine with a mat. Input from a routine and input from a user may cause a processor to change a display and/or haptic element of the mat to encourage a user to complete a routine properly.

A processor may perform a method that includes, for example, receiving an indication of a routine. The method may include determining a body weight and/or size of a user based on input from sensors of a mat and/or input form a user (e.g., through an application or other interface, through a sensor, etc.). Based on a routine and a determined a body size and/or weight, the processor may determine a desired potion of the user and control elements of a mat to indicate the desired position. The processor may receive indications of an actual position of the user and may determine a difference between an actual and a desired position. Based on the difference, the processor may control elements of the mat to indicate to the user a change in position to achieve the desired position (e.g., haptic feedback, display feedback) the processor may determine a next desired position. Based on a current user position and a next desired position, the processor may control the mat to indicate to the user a change in position.

Exercise Room

Figure 16:
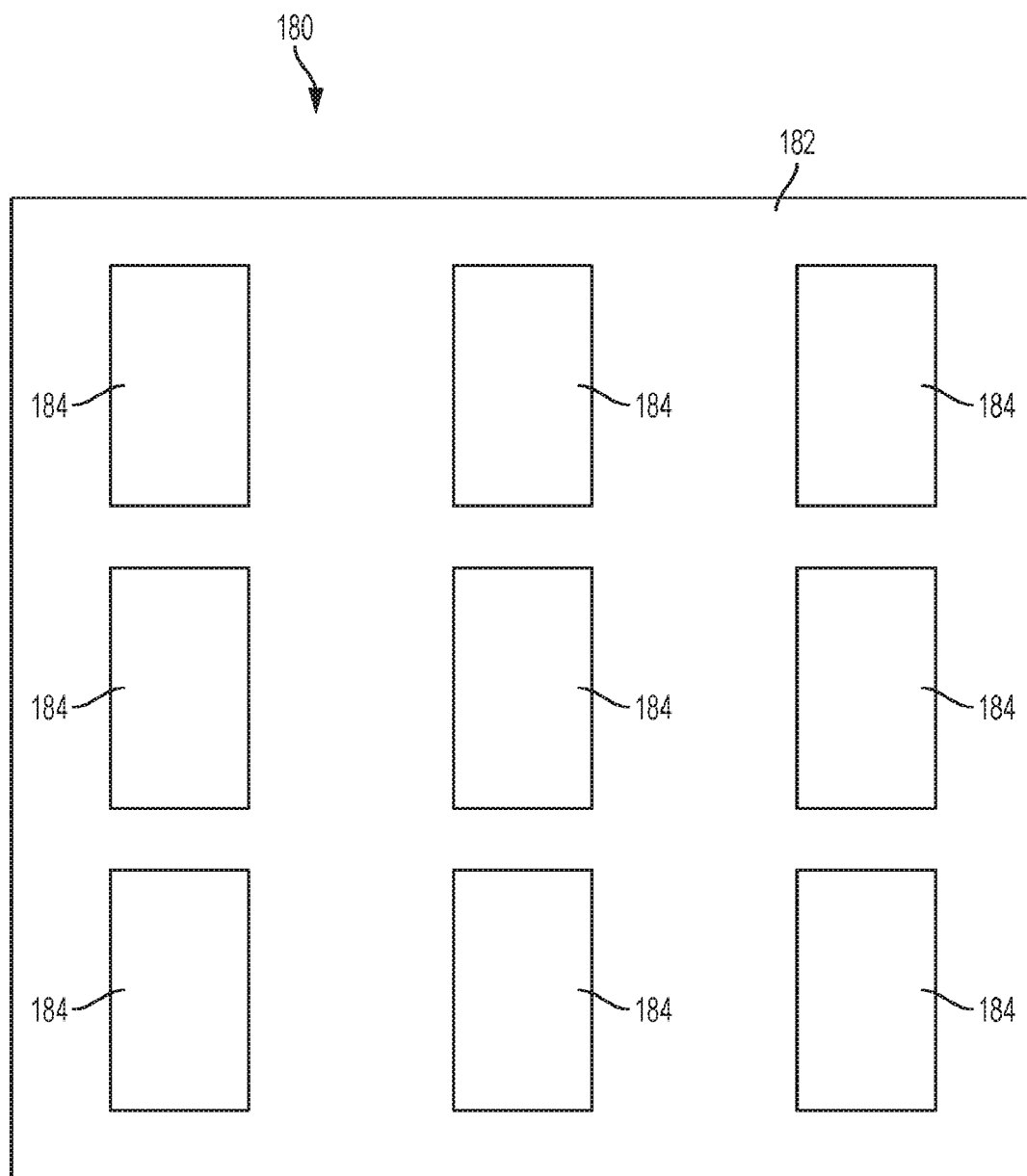
FIG. 16 is a top, plan view of an exercise room according to an embodiment of the present disclosure.

In some embodiments of exercise system 100, for example, as illustrated in FIG. 16, the floor 182 of an exercise room 180 may include P/F/ sensors 108, displays 110, and/or actuating mechanisms 112. For example, P/F/ sensors 108, displays 110, and/or actuating mechanisms 112 may be embedded in floor 182 of exercise room 180. In some embodiments, the entire floor 182 of the exercise room includes a single large display 110. In other embodiments, the floor 182 of the exercise room may instead include a plurality of displays 110 in a similar manner to exercise mat 100 as described above. The surface of floor 182 may include P/F/ sensors 108, displays 110, and/or actuating mechanisms 112. Alternatively, only specific portions 184 of floor 182 may include P/F/ sensors 108, displays 110, and/or actuating mechanisms 112. For example, P/F/ sensors 108, displays 110, and/or actuating mechanisms 112 may only be included at the portions 184 of floor 182 where individual users will be performing an exercise routine.

The surface of floor 182 may be sealed or hardened to provide protection to displays 110, for example, using polyurethane, oil based sealants, paints, or other similar sealing methods. Alternatively or additionally, the surface of floor 182 may include a transparent layer of foam, silicone or other material similar to those mentioned above for exercise mat 100 to provide users with a comfortable exercise surface.

P/F/ sensors 108, displays 110, and/or actuating mechanisms 112 of exercise room 180 may be wired or wirelessly connected to one or more of processors 102, such that an instructor may control the outputs to each portion 184 of floor 182. For example, using a computer, tablet, or other similar device, an instructor may select the current pose to be performed and transmit that selection to each portion 184 for use by a particular student. Processor 102 may control each portion 184 individually to perform the functions describe above with respect to exercise mat 113. Alternatively, each portion 184 may include its own processor 102 for providing the above mentioned features of exercise mat 113. The instructor may also or alternatively select different poses for each portion 184. For example, the instructor may select a modified pose for sending to a particular portion 184 that is in use by a novice student, while sending a regular, non-modified pose to the remaining portions 184 for the rest of the class.

Projection

Figure 17:
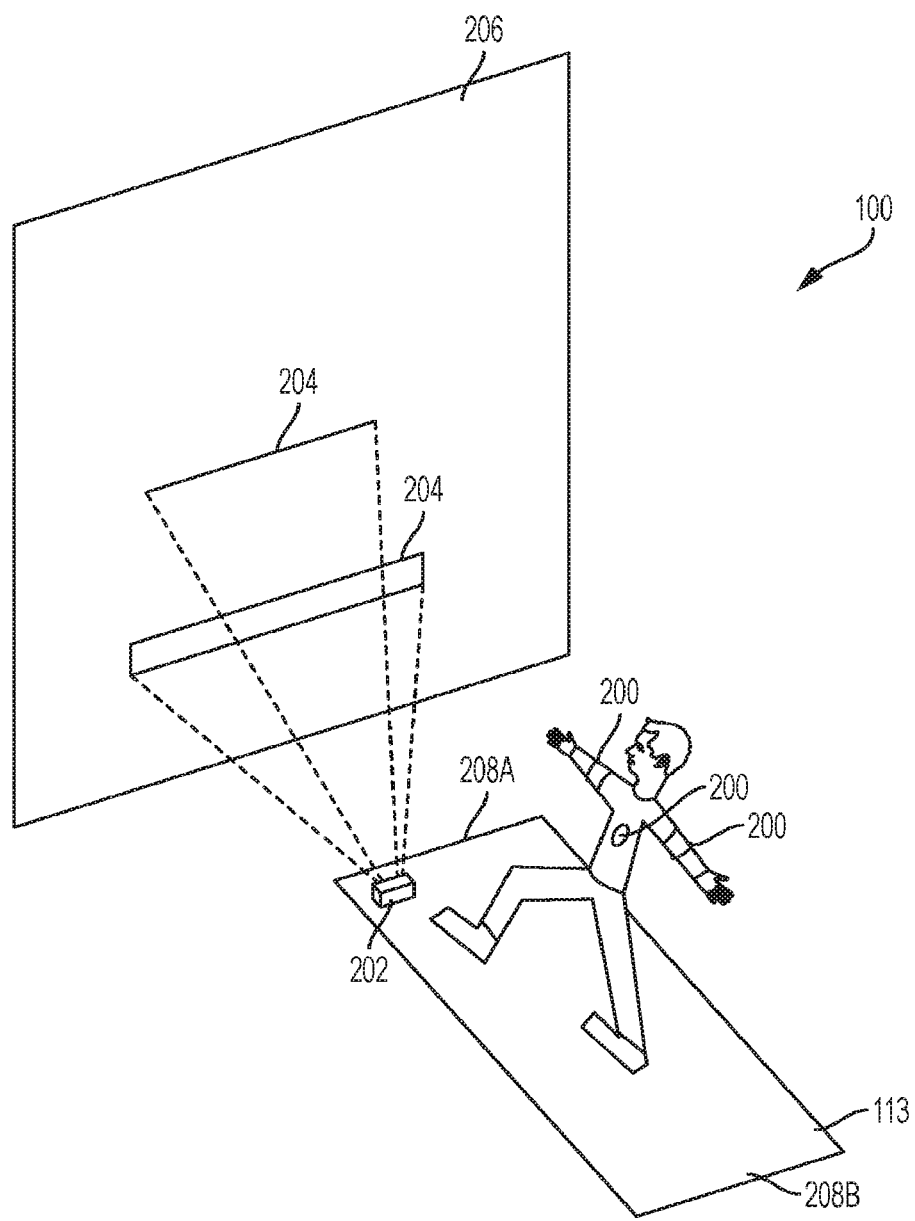
FIG. 17 is a perspective view of an embodiment of the exercise system of FIG. 1 illustrating indications projected on a surface.

In some embodiments, as illustrated in FIG. 17, exercise system 100 may also or alternatively include one or more orientation tracking devices 200 and projection devices 202.

Orientation tracking devices 200 may be attached or secured to body parts of the user. In some embodiments, the user may attach multiple orientation tracking devices 200 to their apparel or body part, for example, an orientation tracking device 200 may be attached to each arm, leg, hand, food, the user's neck, head, torso, hips, etc., or portion thereof. Orientation tracking devices 200 may be attached directly to the user's body part or may be attached to the user's apparel. For example, orientation tracking devices 200 may be attached via hook and loop fasteners (e.g., Velcro® brand fasteners), adhesives, clips, fasteners, or other similar methods of attachment. Orientation tracking devices 200 may also or alternatively be positioned within a pocket of the user's apparel, integrated into the user's apparel, or other similar apparel based forms of attachment. For example, orientation tracking devices 200 may be integrated into or attached to a headband, arm band, shirt, shorts, belt, shoes, socks, gloves, hat, or other similar apparel items.

Orientation tracking devices 200 may be configured to wirelessly communicate with processor 102 via network interface 106. For example, orientation tracking devices 200 may use Bluetooth, WIFI, or other similar forms of wireless communication technologies to communicate with processor 102.

Orientation tracking devices 200 are configured to sense both the position and orientation of the user's body parts and transmit data corresponding to the position and orientation to processor 102 for processing. Examples of position and orientation tracking technologies can be found in U.S. Pat. Nos. 5,600,330; 6,188,355; 6,615,155; 7,555,330; 7,969,143; 8,736,258; and 8,618,795, the entirety of each of which is incorporated herein by reference. Orientation tracking devices 200 may utilize any of the technologies provided in the above referenced patents or any other technology suitable for tracking the position and orientation of the user's body parts.

Projection devices 202 may be any device capable of projecting indications 204, for example, images, lines, shapes or any other indication onto a surface for viewing by the user. For example, projection devices 202 may include video projectors, LED projectors, laser projectors, or other similar types of projectors. Projection devices 202 may be integrated into exercise mat 113, may be included in exercise system 100 as standalone devices, may be included in exercise system 100 as both integrated and standalone devices at the same time. For example, exercise mat 113 may include an integrated projection device 202 and an additional projection device 202 may also be provided separate from exercise mat 113.

Projection devices 202 may project indications 204 on a surface 206 that is visible to the user. Surface 206 may include, for example, walls, ceilings, floors, other students, movable screens, or any other surface that capable of receiving the indications from projection devices 202. Projection devices 202 may be configured to project the indication 204 in a single direction, for example, in the direction of the front 208A of the mat, rear 208B of the mat, toward a specific side of the mat, or any other similar direction. Projection devices 202 may also or alternatively be configured to project the indication in a 360 degree arc around the mat such that the user may view the projection regardless of which direction their head is facing. An example of a 360 degree laser device is disclosed in U.S. Pat. No. 6,332,276, the entirety of which is incorporated herein by reference.

Figure 18A:
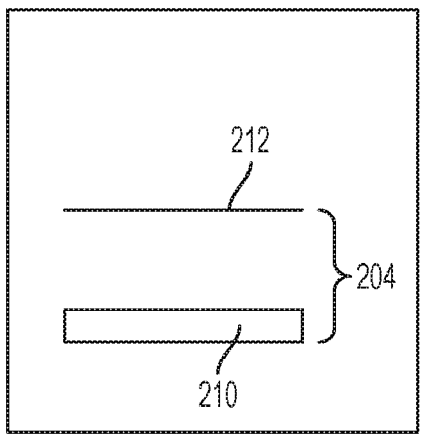
FIGS. 18A-18C are plan views of the surface of FIG. 17 according to embodiments of the exercise system of FIG. 17.
Figure 18B:
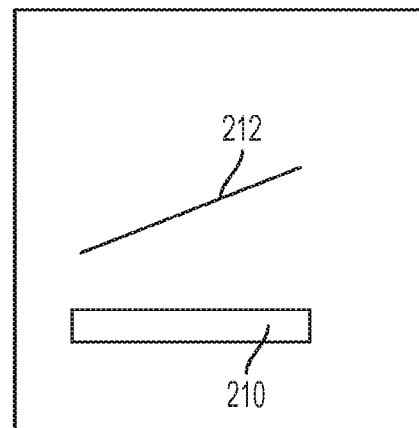
Figure 18C:
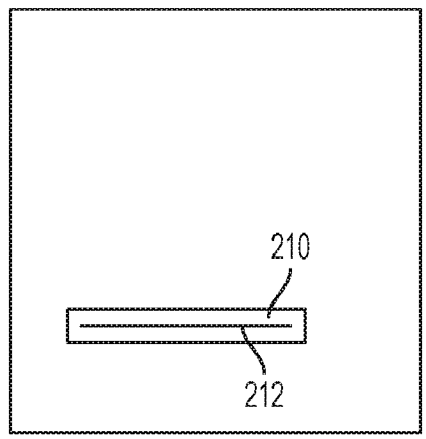

Referring now to FIGS. 18A-18C, in some embodiments, projection devices 202 are configured to project a pair of indications 204. For example, projection devices 202 may project indications 204 of both the desired orientation 210 of the user's body part for the current form or pose that the user is trying to achieve and the current orientation 212 of the user's body part relative to the desired orientation 210. In this embodiment, the projection of the desired orientation 210 is represented as a rectangle and the projection of the current orientation 212 is represented as a line. It is contemplated that any other combination of shapes, lines, dots, etc., may be used.

During use, the projection of the desired orientation 210 remains static while the projection of current orientation 212 is adjusted based on the data received from the orientation tracking device 200 of the respective body part. In an example embodiment, as illustrated in FIG. 18A, the projection of the current orientation 212 is parallel to the projection of the desired orientation 210. This may indicate that the user's body part, for example, the user's chest, is facing the desired direction. The projection of the current orientation 212 is also offset and spaced apart from the desired orientation 210. This may indicate, for example, that the user's body part although facing the desired direction is also tilted away from the desired orientation. For example, the user's chest may be tilted too far toward the back 108B of exercise mat 113 rather than being centered over the user's hips. In another example, as illustrated in FIG. 18B, the projection of the user's current orientation 212 is both offset from the projection of the desired orientation 210 and angled relative to the projection of the desired orientation 210. This may indicate, for example, that the user's body part is both titled and twisted relative to the desired orientation. For example, where the desired orientation of the user's chest is centered over the user's hips and facing toward the front 108A of the exercise mat, a projection of the user's current orientation 212 as illustrated in FIG. 18B may indicate that the user's chest is actually turned toward a side of exercise mat 113 and tilted toward the back 108B of exercise mat 113. As the user adjusts the orientation of the body part associated with the orientation tracking device 200, the orientation tracking device 200 senses the orientation and position of the body part and transmits updated data to processor 102 for processing. Based on the updated data, the projection of the current orientation 212 is adjusted by processor 102, for example, by rotating the line and/or moving the line closer to or father from the projection of the desired orientation 210. Once the user has adjusted the orientation and position of the body part to coincide with the desired orientation, the projection of the current orientation 212 will overlap with the projection of the desired orientation 210, as illustrated, for example, in FIG. 18C.

Projections 210 and 212 provide the user with an easy and intuitive instruction for how to adjust their pose or form to coincide with the pose or form required by the exercise. For example, where the user would normally watch an instructor and then try to assume the same pose or form as the instructor, which often fails to provide a user with an understanding of the proper pose or form, all the user needs to do using this embodiment of exercise system 100 is adjust the body part until the projection of the current orientation 212 matches the projection of the desired orientation 210. This allows the user to reduce the assumption of the pose or form to a simple binary problem, similar to a game. For example, a game of how do I get the line into the box. The line is either in the box, i.e., the proper form or pose has been achieved, or outside of the box, i.e., adjustment is still necessary to achieve the proper form or pose.

In some embodiments, orientation tracking devices 200 and projection devices 202 may provide standalone instruction to a user separate from the P/F/ sensors 108, displays 110, and/or actuating mechanisms 112 described above for use exercise mat 113. For example, orientation tracking devices 200 and projection devices 202 may be used with a normal exercise mat or no exercise mat at all. In other embodiments, orientation tracking devices 200 and projection devices 200 may be used in conjunction with P/F sensors 108, displays 110, and/or actuating mechanisms 112, where, for example, P/F sensors 108, displays 110, and/or actuating mechanisms 112, may be used to assist the user in positioning their feet, hands, knees, etc. at the correct locations on the exercise mat 113 while orientation tracking devices 200 and projection devices 202 may assist the user in achieving the proper orientation and position of one or more body parts that are not in direct contact with exercise mat 113. In this manner, exercise system 100 may provide a user with improved instruction in the proper forms or poses of an exercise without requiring direct intervention by an instructor.

Further Embodiments

The above described features of exercise system 100 may also be applied to other exercise fields including, for example, baseball, golf, football, hockey, or any other exercise activity. For example, the grip on a golf club may include P/F sensors, displays, actuators, orientation tracking devices, and/or other similar features to show a user how to hold the grip, whether the user's grip is balanced, whether the golf club is held in the proper orientation before, during, and after the swing, and/or other similar feedback. Additionally or alternatively, the user's glove may include P/F sensors, displays, actuators, orientation tracking devices, and/or other similar features to show the user where on their hand the grip needs to be positioned, and whether the hand is being held in the proper orientation during, before, and after a swing. Projection devices may also be included to provide the user with visual feedback of their orientation before, during, and after a swing.

Similarly, a football or glove may include P/F sensors, displays, actuators, orientation tracking devices, and/or other similar features to provide a user with feedback on grip, finger spacing, etc. of a football, to assist the user in obtaining the proper grip for throwing, etc. For example, P/F sensors, displays, actuators, and/or orientation tracking devices, may assist running backs and receives with proper methods for carrying the ball to avoid fumbles by showing the running back or receiver how much force/pressure is being applied to the ball during a carry, what the orientation of the ball or user's hand is during a carry, and whether there are any weak spots in the carry that could allow the ball to be knocked out of their hands. For example, the P/F sensors, displays, and/or actuators may be used to determine whether the running back or receiver's hands, chest, arm, etc. are exerting even and/or opposing forces on the ball to maintain the ball within their control. When the running back or receiver has the ball in a carry posture that is unbalanced, for example, because the forces exerted by the player on the ball do not even out, the displays/actuators may indicate this fact to the user and indicate a likely direction in which the ball will escape from their grasp, potential corrections to their carry, or other similar indications. The features of exercise mat 100 could also be used for military training, with non-stable training simulators (i.e. skiing simulators), in pools, or any other situation that may require instruction.

In still other embodiments, any surface, item and/or wearable piece may have a haptic and/or display element that guides a user in an activity. For example, a car seat, office chair, etc. may guide a user into a proper ergonomic seating position. As another example, a glove may guide a surgeon into a proper tool holding position. As another example, a surgical tool itself may guide a hand into a proper holding position.

While the foregoing invention has been described in some detail for purposes of clarity and understanding, it will be appreciated by one skilled in the art, from a reading of the disclosure that various changes in form and detail can be made without departing from the true scope of the invention.

What is claimed is:

1. A system comprising:
a surface;
at least one sensor coupled to the surface, in which the at least one sensor is configured to sense when a force is applied to a respective portion of the surface;
at least one display at least partially embedded into the surface and configured to display at least one indication corresponding to a desired location for a body part of a user in accordance with a routine;
at least one processor configured to control:
displaying on the at least one display the at least one indication corresponding to the desired location for the body part of the user in accordance with the routine;
receiving sense data indicating sensing by the at least one sensor an application of force to the surface;
determining whether a location of the sensed application of force is different from a display location of the at least one indication; and
in response to determining that the location is different, displaying on the at least one display at least one indicator indicating a direction from the location of the sensed application of force to the display location of the at least one indication.

2. The system according to claim 1, wherein the at least one processor is configured control:
receiving second sense data indicating sensing by the at least one sensor a change in the location of the application of force to the surface to a changed location;
determining that the changed location corresponds to the display location of the at least one indication; and
displaying on the at least one display an indication of a match between the changed location and the display location of the at least one indication.

3. The system according to claim 1, wherein the surface includes a mesh, and wherein the at least one display is secured to the mesh.

4. The system according to claim 1, wherein the at least one indicator is in an inactive state when the location of the sensed application of force corresponds to the location of the at least one indication.

5. The system according to claim 4, wherein the at least one indicator is transitioned to an active state when the location of the sensed application of force is different from the location of the at least one indication.

6. The system according to claim 1, wherein the at least one indicator is highlighted when in an active state.

7. The system of claim 1, further comprising:
a projector, and
in which the at least one processor is configured to control projecting by the projector a display indicating a positional adjustment of the user.

8. The system of claim 1, wherein the surface is a surface of at least one of: a ball, a club, a glove, a chair, or an exercise mat.

9. The system of claim 1, wherein the routine comprises at least one of:
an exercise routine or a sporting routine.

10. A system comprising:
a surface;
at least one actuating mechanism coupled the surface, the at least one actuating mechanism actuatable to deform at least a portion of the surface corresponding to a desired location for a body part of a user in accordance with a routine;
at least one processor configured to control:
actuating the at least one actuating mechanism to cause a deformation in the surface corresponding to the desired location for the body part of the user in accordance with the routine.

11. The system of claim 10, wherein the at least one actuating mechanism includes at least one of a bladder or actuator.

12. The system of claim 11, further comprising:
at least one pump in fluid communication with the bladder, wherein the at least one processor is configured to control:
activating the at least one pump to supply or withdraw fluid from the bladder to cause the deformation corresponding to the desired location for the body part of the user.

13. The system of claim 10, wherein the at least one actuating mechanism comprises at least one of a solenoid, an electric motor, a hydraulic motor, or a pneumatic motor.

14. The system of claim 10, further comprising:
at least one sensor configured to sense when a force is applied to a respective portion of the surface.

15. The system of claim 14, wherein the at least one processor is configured to control:
receiving sense data indicating sensing by the at least one sensor an application of force to the surface;
determining that a location of the sensed application of force is different from a location of the deformation; and
actuating the at least one actuating mechanism to cause a deformation in the surface identifying a direction from the location of the sensed application of force to the location of the deformation corresponding to the desired location for the body part of the user.

16. The system of claim 15, wherein the at least one processor is configured to control:
receiving second sense data indicating sensing by the at least one sensor a second application of force to the surface;
determining a weight distribution of the user based at least in part on the sensed second application of force; and
actuating the at least one actuating mechanism to cause a second deformation in the surface at a location corresponding to a location of the sensed second application of force, the second deformation applying an additional force to a body part of the user applying the sensed second application of force to the surface, an amount of the additional force being based at least in part on the weight distribution.

17. The system of claim 16, wherein the at least one processor is configured to control:
receiving third sense data indicating a change in the second application of force to the surface;
determining a change to the weight distribution of the user based at least in part on the change in the second application of force to the surface; and
adjusting the amount of the additional force applied by the at least one actuating mechanism by an amount corresponding to the change to the weight distribution of the user.

18. The system of claim 17, wherein a rate at which the additional force is applied is based at least in part on a difference between the weight distribution of the user and a desired weight distribution of the user in accordance with a form of the routine.

19. The system of claim 18, wherein the rate at which the additional force is applied is increased or decreased as the difference between the weight distribution of the user and the desired weight distribution of the user increases or decreases respectively.

20. The system of claim 10, further comprising at least one display at least partially disposed between the at least one actuating mechanism and the surface.

* * * * *